(12) United States Patent
Ostroff (10) Patent No.: US 8,423,136 B2
(45) Date of Patent: Apr. 16, 2013

(54) METHODS AND IMPLANTABLE DEVICES FOR INDUCING FIBRILLATION BY ALTERNATING CONSTANT CURRENT

(75) Inventor: Alan H. Ostroff, San Clemente, CA (US)

(73) Assignee: Cameron Health, Inc., San Clemente, CA (US)

( * ) Notice: Subject to any disclaimer, the term of this patent is extended or adjusted under 35 U.S.C. 154(b) by 960 days.

(21) Appl. No.: 12/494,637

(22) Filed: Jun. 30, 2009

(65) Prior Publication Data

US 2009/0270932 A1    Oct. 29, 2009

Related U.S. Application Data

(62) Division of application No. 11/114,526, filed on Apr. 26, 2005, now Pat. No. 7,555,338.

(51) Int. Cl.
*A61N 1/39* (2006.01)
(52) U.S. Cl.
USPC .......................... 607/5; 607/2; 607/4
(58) Field of Classification Search ............ 607/2, 4, 607/5
See application file for complete search history.

(56) References Cited

U.S. PATENT DOCUMENTS

| 4,375,817 | A | * | 3/1983 | Engle et al. | 607/4 |
| 5,215,083 | A | | 6/1993 | Drane et al. | |
| 5,609,618 | A | * | 3/1997 | Archer | 607/74 |
| 5,649,971 | A | | 7/1997 | Fain et al. | |

OTHER PUBLICATIONS

International Preliminary Report on Patentability and Written Opinion, Oct. 30, 2007, PCT/US2006/014670.

* cited by examiner

*Primary Examiner* — Carl H Layno
*Assistant Examiner* — Jennifer Ghand
(74) *Attorney, Agent, or Firm* — Schwegman Lundberg & Woessner, P.A.

(57) ABSTRACT

Devices configured for and methods for inducing fibrillation in a patient using a controlled current AC signal applied via electrodes of an implanted ICD. In some embodiments, the AC signal is applied as a series of alternating constant current pulses. Some embodiments make use of a specialized H-bridge circuit for applying the AC signal. A low-side current controlling portion of an ICD's circuitry may make up part of the specialized H-bridge circuit. Further embodiments include devices embodying these methods.

6 Claims, 6 Drawing Sheets

METHODS AND IMPLANTABLE DEVICES FOR INDUCING FIBRILLATION BY ALTERNATING CONSTANT CURRENT

RELATED APPLICATIONS

This application is a divisional of U.S. patent application Ser. No. 11/114,526, filed Apr. 26, 2005 and titled METHODS AND IMPLANTABLE DEVICES FOR INDUCING FIBRILLATION BY ALTERNATING CONSTANT CURRENT, now U.S. Pat. No. 7,555,338, the disclosure of which is incorporated herein by reference.

This application is related to U.S. patent application Ser. No. 10/011,955, filed Nov. 5, 2001, now U.S. Pat. No. 6,952,608 and titled DEFIBRILLATION PACING CIRCUITRY, which has a continuation filed as U.S. patent application Ser. No. 11/146,607, on Jun. 7, 2005, now U.S. Pat. No. 7,522,957, and a further continuation filed as U.S. patent application Ser. No. 12/426,779, on Apr. 20, 2009, both titled DEFIBRILLATION PACING CIRCUITRY. The disclosures of these aforementioned applications are incorporated herein by reference.

FIELD

The present invention is related to the field of electric cardiac therapy. More particularly, the present invention is related to methods and devices for inducing fibrillation with implantable medical devices.

BACKGROUND

An implantable cardioverter-defibrillator (ICD) is an implantable device designed to deliver life saving defibrillation therapy to a patient in response to potentially deadly cardiac malfunctions. Often, when an ICD is implanted, it is tested to determine whether it can function for its purpose by observing whether the ICD can provide a shock exceeding the patient's defibrillation threshold (DFT). To perform this test, the ICD is implanted and the patient's heart is caused to fibrillate in the controlled environment of an operating room. Once fibrillation is induced, the ICD is expected to shock the patient back to a normal rhythm. If so, the ICD passes at least one round of the test. This procedure may be repeated. If the ICD fails to return the patient to normal rhythm, an attending physician will take steps, such as the use of an external defibrillator, to bring the patient's heart back to normal rhythm. After failure, the ICD is normally discarded, and the procedure may be aborted or a different ICD may be used.

SUMMARY

The present invention is directed toward methods and devices for inducing fibrillation in a patient using a controlled current AC signal applied via an implanted ICD. In some embodiments, the AC signal is applied as a series of alternating constant current pulses. Some embodiments make use of a specialized H-bridge circuit for applying the AC signal. A low-side current-controlling portion of the illustrative ICD's circuitry may make up part of the specialized H-bridge circuit. Further embodiments include devices embodying these methods.

DETAILED DESCRIPTION

The following detailed description should be read with reference to the drawings. The drawings, which are not necessarily to scale, depict illustrative embodiments and are not intended to limit the scope of the invention. As used herein, a switch is considered open when it does not allow current to flow therethough (as in an open circuit), and closed when current is allowed to flow. As further discussed below, switches may also modulate current flow.

Several methods for inducing fibrillation for the purpose of testing an implantable cardioverter-defibrillator (ICD) have been tried. See, for example, U.S. Pat. No. 5,643,323 to Kroll et al. Initially, when devices were implanted transthoracically, ready access to the myocardium was established during implantation. From a wall outlet, with a voltage step-down, a 1 to 20 volt AC signal at 50/60 hertz could be applied directly to heart tissue to induce fibrillation.

With less invasive and/or non-transthoracic implantations, new techniques were developed. In one such technique, a catheter was introduced to the heart and fibrillation could then be induced using, again, an AC signal at 50/60 hertz. The catheter, however, represented an added complication to the procedure.

For convenience, other techniques relying on the ICD itself were developed. Overdrive pacing, where the heartbeat is captured and then pacing pulses are applied at steadily higher rate, is one approach. Another approach is to apply a pulse at a time corresponding to the patient's T-wave. A third ICD-based approach is to apply a long pulse that exceeds the cardiac cycle period. Each of these approaches has its shortcomings, as discussed by Kroll et al. in U.S. Pat. No. 5,643,323.

Kroll et al. indicates the use of a "continuous charging" method during application of a fibrillation inducing signal that may be supplied as a single long pulse or a pulse train in the form of a series of pulses of opposing polarity. In particular, power flows through the defibrillation capacitors, which are not charged in advance, and the charging transformer directly drives the output signal. This introduces a number of extraneous reactive impedances into the output signal. The output is not controlled, and is therefore imprecise. If the applied signal fails to induce fibrillation, it will likely be repeated. Application of the fibrillation inducing signal drains battery power and is likely noticeable (and discomforting) to a patient. As a result of these factors, a more precise fibrillation inducing signal is desired.

An illustrative embodiment of the present invention provides an ICD-based method of applying a constant current AC signal to a patient's heart to induce fibrillation. The constant current AC signal comprises a series of alternating positive and negative current pulses having substantially the same magnitude, both from pulse to pulse, as well as within each pulse. Power to keep the signal constant comes from the defibrillating capacitors which, prior to applying the fibrillating signal, are charged to a predetermined level sufficient for keeping the output constant. Once charged to a desired and/or sufficient degree, the energy storage system is used to provide a voltage/current source for a controlled current fibrillation inducing method. For purposes herein, a fibrillation-inducing current is considered "constant" if it is, within a reasonable range, generally independent of patient and/or lead impedance.

The constant current AC signal can be controlled using a transistor operating linearly such that current flow may be controlled or modulated by changing a control signal supplied to the transistor. Examples of transistors having such modes of operation include a field effect transistor, such as a MOSFET, and bipolar transistors such as a bipolar junction transistor or an insulated gate bipolar transistor (IGBT). Those of skill in the art will readily identify other structures that may perform in a similar or otherwise suitable fashion to control current.

The fibrillation inducing pulse is intended to disrupt tissue electrical activity that regulates muscle contraction. Current density can be a useful metric for indicating whether a given pulse will induce fibrillation. Maintaining a constant current, rather than outputting a particular voltage, may assure that a device, regardless of individual patient physiology/impedance, reliably induces a desired level of current density and, as a result, fibrillation.

Figure 1:
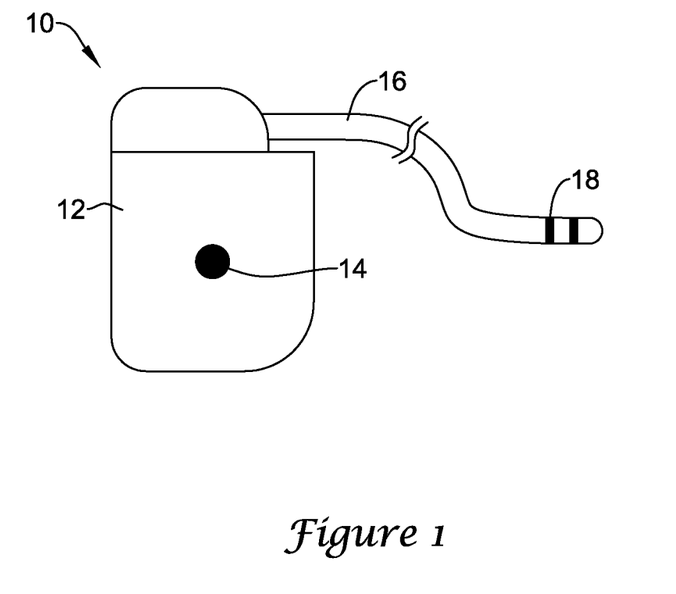
FIG. 1 is a schematic plan view of an ICD including a lead assembly.

FIG. 1 is a perspective view of an ICD including a lead assembly. The ICD 10 includes a canister 12 having an optional canister electrode 14 disposed thereon. A lead assembly 16 extends from the canister 12, and includes one or more electrodes 18 which may be used as shocking or sensing electrodes, or both. If desired, such an ICD may be provided in the conventional manner, including placement of the canister 12 in the patient's torso and advancement of the lead assembly 16 through the patient's vasculature to a location adjacent heart tissue or within the heart. In other embodiments, the ICD is placed subcutaneously. Examples of methods and devices for, and associated with, subcutaneous placement are illustrated in U.S. Pat. Nos. 6,788,974; 6,754,528; 6,721,597; and 6,647,292, which are assigned to the assignee of the present invention and the disclosures of which are all incorporated herein by reference.

The lead assembly 16 includes conductive elements therein for providing electrical conduction between the electrodes 18 and the canister 12. The canister 12 houses a battery and circuitry for detecting when fibrillation is occurring, and for providing a defibrillation shock.

Figure 2:
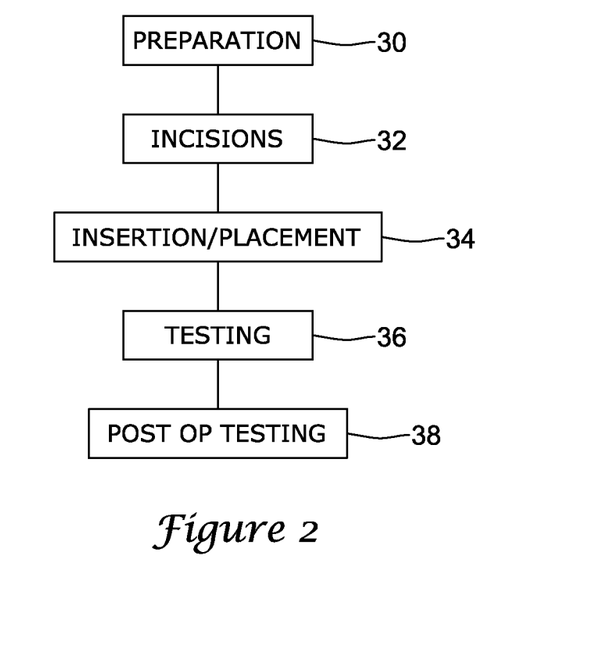
FIG. 2 is a block diagram illustrating the process of ICD implantation.

FIG. 2 is a block diagram illustrating the process of ICD implantation. An ICD such as ICD 10 (FIG. 1) may be implanted by the following manner. First the patient is prepared 30 for implantation by creating a sterile field for placement, and, if necessary, application of general anesthesia and/or local numbing agent. Next, one or more incisions 32 are made, and the ICD/lead assembly is inserted and placed internal to the patient, as shown at 34. The lead assembly is advance to an appropriate location. Next, the ICD is tested 36 to make certain it works properly. This testing 36 may include the inducement of fibrillation and observation of whether the ICD acceptably defibrillates the patient. Finally, post-operative testing 38 may also take place. For example, within three to six months of implantation, the ICD may be tested again to determine whether physiological changes (for example, the development of scar tissue or fibroids around implanted electrodes), or other circumstances later impede ICD function.

Figure 3:
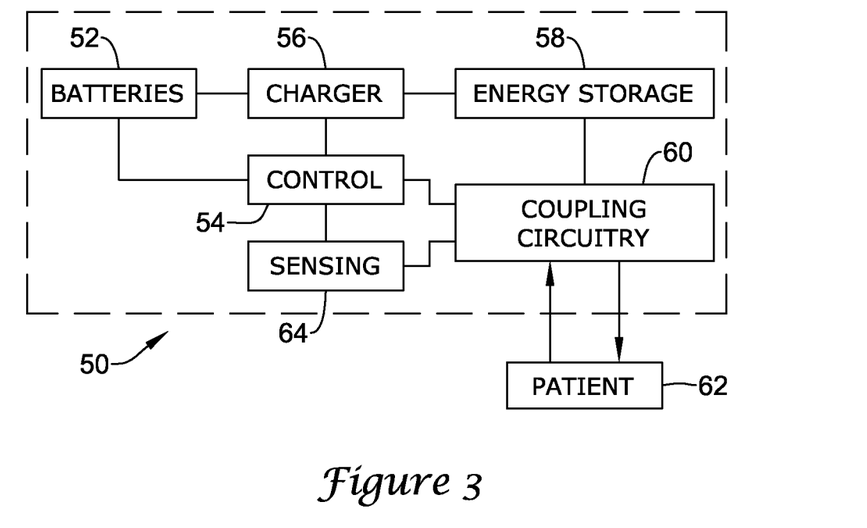
FIG. 3 is a block schematic for an ICD.

FIG. 3 is a block schematic for an ICD. The ICD 50 typically includes batteries 52 that power a control block 54, which may include a microcontroller, logic, or the like. The control block 54 is coupled to a charger 56 that is used to relay power from the batteries 52 to energy storage 58. Energy storage 58 is a temporary energy storage system that may include one or more capacitors. The charger 56 is used to step up the voltage supplied by the batteries 52 (typically in the range of a few volts) to a voltage more suitable for defibrillation (often on the order of hundreds of volts), and store this energy at the higher voltage in the energy storage 58. The energy storage 58 is electrically connected to coupling circuitry 60 that is used to connect with the patient 62. Sensing circuitry 64 is also connected to the coupling circuitry 60, and is used by the control block 54 to determine whether defibrillation is needed. The sensing circuitry 64 may include suitable circuitry and circuit elements for amplifying, filtering, and/or analysis of cardiac signals.

The typical operation of an ICD for defibrillation includes the following. First, the control block 54 determines, using the sensing circuitry 64, that defibrillation is needed due to the occurrence of a malignant cardiac condition. Next, the control block 54 causes the charger 56 to begin charging the energy storage 58. Once the energy storage 58 is charged to a desired level or for a predetermined time, the control block 54 causes the coupling circuitry 60 to discharge the energy storage 58 to the patient 62.

Figure 4A:
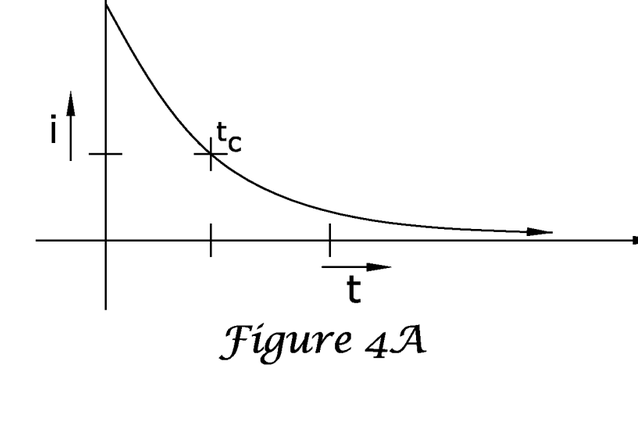
FIGS. 4A-4C graphically illustrate energy storage and output for several configurations.
Figure 4B:
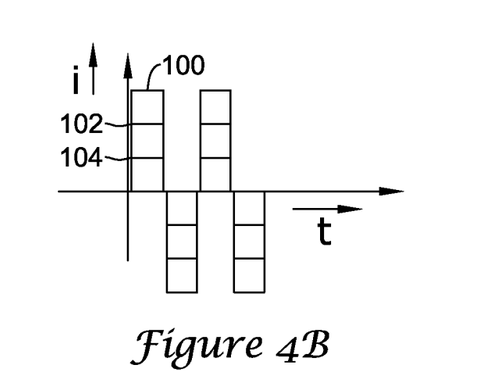
Figure 4C:
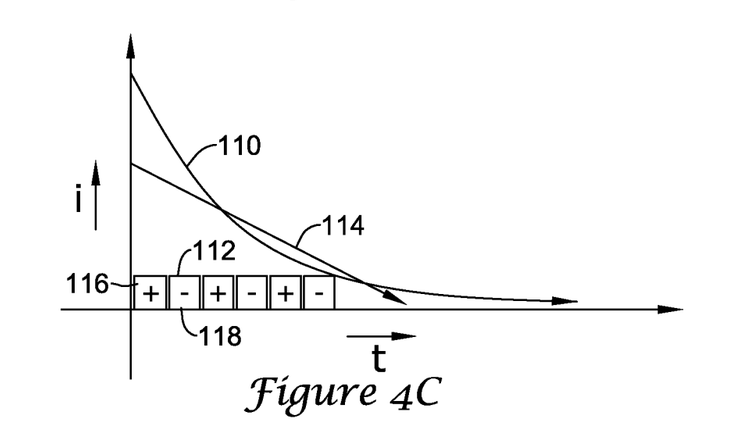

FIGS. 4A-4C illustrate example output waveforms for certain fibrillation inducing waveforms. FIG. 4A shows an output current waveform over time for a typical ICD when a long pulse is emitted from a charged capacitive energy storage system. Assuming, for example, at 125 µF capacitance and a 50 ohm load resistance, a time constant of 6.3 milliseconds would occur. This means that within 6.3 milliseconds of closing the switches to discharge the capacitance, 63% of the stored charge would be discharged, shown at point tC. This discharge is quick and is not controlled, particularly because the load impedance varies from patient to patient.

FIG. 4B illustrates another uncontrolled output. In this example, a steady voltage is applied across a varying load. Such an example illustrates what may happen when a voltage output fibrillation-inducing signal is applied to different patients having different internal impedances. Three different current signals are shown 100, 102, 104. Signal 100 significantly larger than the amplitude of signal 102, which is still larger than signal 104. The three signals 100, 102, 104 can be produced using the same voltage output applied across three different impedances. For example, in some patient populations the impedance between implanted electrodes may vary for a subcutaneous system between 25-200 ohms. With respect to causing fibrillation in a patient, a system using such an uncontrolled output may need to be designed such that the smallest magnitude current, signal 104, is sufficient to cause fibrillation. This causes an unnecessarily large signal to be applied for some patients. With respect to the system proposed by Kroll et al. in the '323 patent, the voltage output under consideration would be the charger output voltage, as attenuated by the intervening power capacitors and whatever other circuit elements are in the current path.

FIG. 4C is a graph comparing energy storage and output signal for an illustrative embodiment. A first line 110 illustrates voltage remaining on a power capacitor during an uncontrolled discharge after high-voltage charging (similar to that shown in FIG. 4A), a second line 112 is shown representing current delivered to the patient using a controlled discharge in accordance with an illustrative embodiment, and a third line 114 illustrates the voltage remaining on a power capacitor during the controlled discharge using line 112. Within line 112, the + blocks 116 represent a first polarity of current delivery, and the − blocks 118 illustrate a second polarity for current delivery. Small blank periods are shown between + blocks and − blocks to allow the device to safely switch polarities. Each block may be about ten milliseconds in duration, though specific durations may vary.

Figure 5:
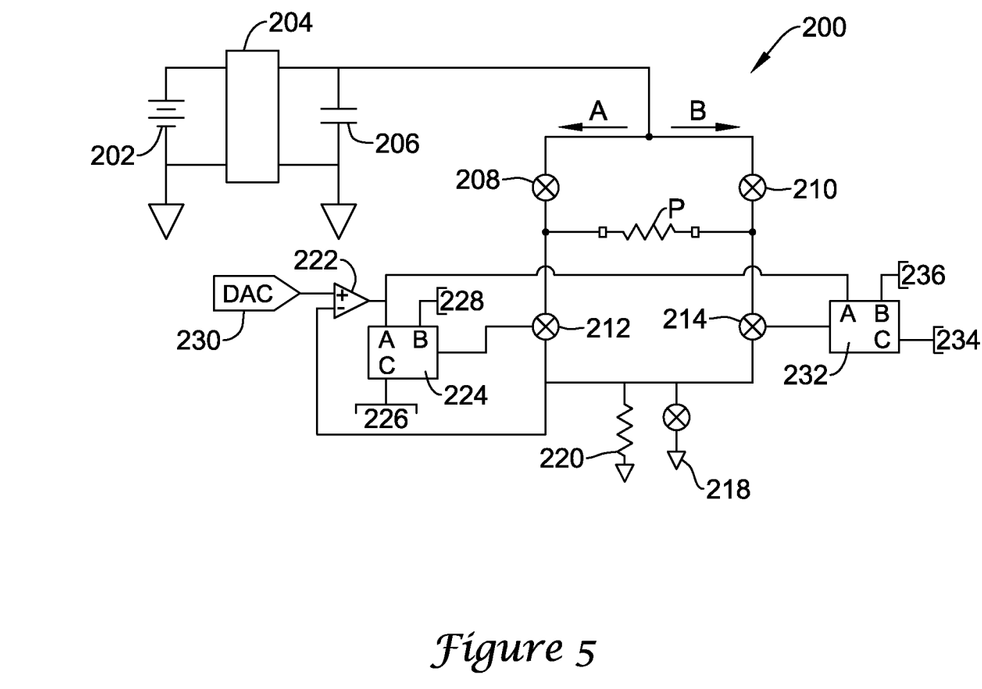
FIG. 5 is a schematic diagram for an illustrative embodiment.
Figure 6:
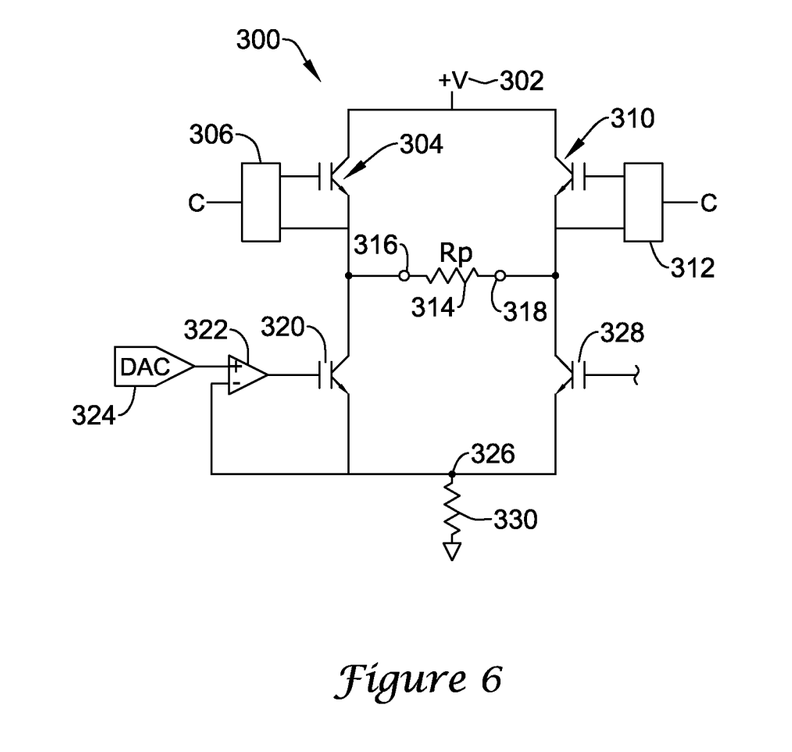
FIG. 6 is a simplified schematic diagram for another illustrative embodiment.

For the illustrative embodiment, it can be seen that the voltage remaining on the capacitor during controlled discharge (line 114) is reduced in a generally linear manner, while the uncontrolled discharge (line 110) causes voltage reduction in an exponential fashion. Thus, while the uncontrolled capacitor discharge starts at a much higher level, it quickly dissipates such that the controlled discharge provides a larger signal as time goes on. For controlled discharge, the capacitor may be charged sufficiently to allow the device to operate as a constant current source until the fibrillation inducing signal has been delivered. During application of the fibrillation inducing signal, the charger may continue to charge the capacitors. It is believed that delivery of a constant current signal may provide a more reliable fibrillation inducing system. The embodiments illustrated by reference to FIGS. 5-6 are adapted to provide just such an output.

Because patient physiology can vary, the actual amount of energy needed to produce the fibrillation inducing stimulus varies as well. More specifically, the patient impedance can vary, such that the power/energy needed varies in direct proportion thereto, as in $E=P*t=I^2R_p*t$, with $R_p$ being variable from patient to patient, and even sometimes changing at different times due to patient movement or respiration, or differing patient hydration and electrolyte balance. In an illustrative embodiment, a worst-case scenario is estimated or defined, and the capacitor is charged sufficiently to assure constant current can be provided in the defined worst-case scenario. For example, assuming a worst case impedance of about 200 Ohms, and assuming a desired current of 250 mA, then a minimum voltage can be estimated for the capacitor charge depending upon the period of time for which pulses are applied, and the overall capacitance. Thus, if:

$$V_{MIN\ ENDING}=I*Z_{MAX}+V_{SM};$$

$$V=Q/C;\ \text{and}$$

$$\Delta V=\Delta Q/C=I*\Delta t/C;$$

Then:

$$V_{MIN\ START}=V_{MIN\ ENDING}+\Delta V=V_{SM}+I*(Z_{MAX}+\Delta t/C)$$

Where $Z_{MAX}$ is the worst case impedance, $V_{SM}$ is a voltage safety margin, I is the constant current magnitude, $\Delta t$ is the time during which constant current is applied in the entire fibrillation pulse (both positive and negative pulses), and C is the capacitance of the capacitor(s) on which charge is stored for use in the fibrillation inducing pulse. $V_{SM}$ may account for voltage drops occurring across any switches, transistors, or other elements included in the coupling circuitry.

FIG. 5 is a schematic diagram for an illustrative embodiment. A relatively complete embodiment is shown including various additional components that are not necessary to the practice of the present invention. A number of switches are shown without specifying the type of switch being used; any suitable switch including, for example, IGBT, MOSFET, or bipolar junction transistors may be used as switches. FIG. 6 shows a more specific illustrative example including the use of IGBT devices, but excludes certain components that do not aid in the understanding of the example. It should be noted that the "ICD" embodiments shown in FIGS. 5 and 6 are also adapted for use as pacing devices, as further noted below. Thus, the use of the term "ICD" should be understood as implying devices having at least cardioversion or defibrillation functionality, without excluding devices having further functions such as, for example, pacing functionality.

The ICD 200 includes a battery 202 that is coupled to a charger 204. The charger 204 steps up the output voltage of the battery 202 to a level appropriate for charging the high power capacitor 206. While a single high power capacitor 206 is shown, it is understood that element 206 may represent a single or more actual capacitors placed in a suitable configuration.

The capacitor 206 is coupled to a first high side switch 208 and a second high side switch 210. These switches 208, 210 may be controlled in any suitable fashion. A first low side switch 212 and a second low side switch 214 are also shown. Current is directed to the patient, P (shown schematically as an impedance), using two electrodes, with one coupled to the junction of the first high and low side switches 208, 212, and the other coupled to the junction of the second high and low side switches 210, 214.

The first and second low side switches 212, 214 have outputs going to a low side having two outlet legs. A first outlet leg is a defibrillation (DF) leg 218 having a DF switch, and the second outlet leg is a pacing leg 220. During ordinary operation, the DF switch in the first outlet leg 218 is closed, pulling the outputs of the low side switches 212, 214 to ground. This configuration is suited for application of a high voltage defibrillation pulse to the patient P. For a pacing function, the DF switch is open in DF leg 218 such that current is directed through the resistor in the pacing leg 220. Typically the pacing leg resistor will be relatively small but sufficient to allow control over current passing therethrough. In an illustrative embodiment, the resistor in the pacing leg 220 has a resistance in the range of one to five (1-5) ohms, though any suitable resistor may be used. In an illustrative method of inducing fibrillation in the patient, the DF switch 218 is opened.

The first low side switch 212 is controlled by a control signal generated using an operational amplifier 222 through a first multiplexer 224. The first multiplexer 224 has inputs A and B, and control C. The output of amplifier 222 is coupled to input A of multiplexer 224, while another input 228 is generated for input B. In response to a signal 226 applied at control C of multiplexer 224, an output is provided to control the first low side switch 212, the output being selected from inputs A and B. The operational amplifier 222 also provides a control signal that can be used by the second low side switch 214 through a second multiplexer 232. Multiplexer 232 also takes inputs A and B, with input A coming from the operational amplifier 222, and input B being generated as signal 236 from an associated control block. Control C is shown receiving a signal 234 which may also be generated by an associated control block. If desired, signals 226 and 234 may be provided as a single signal in some embodiments.

The control signal from the operational amplifier 222 is generated by the use of a digital to analog converter (DAC) 234 and feedback from the node at the output of the low side switches 212, 214. In particular, the operational amplifier 222 drives whichever low side switch 212, 214 is selected allow sufficient current flow to allow the feedback voltage to equal the voltage output by the DAC 232. The following chart illustrates operation of the system of FIG. 5 and DAC 232 in various modes, with A and B representing the direction of current flow during a given mode:

| Mode | DF - A | DF - B | Pace - A | Pace - B | Induce Fib. A | Induce Fib. B |
|---|---|---|---|---|---|---|
| SW 208 | Closed | Open | Closed | Open | Closed | Open |
| SW 210 | Open | Closed | Open | Closed | Open | Closed |
| Trans 212 | Off | On | Off | Adjustable | Off | Adjustable |
| Trans 214 | On | Off | Adjustable | Off | Adjustable | Off |
| SW- leg 218 | Closed | Closed | Open | Open | Open | Open |
| MUX 224 | B | B | A | A | A | A |
| Control 226 | High | High | Low | Low | Low | Low |
| Input 228 | Low | High | N.A. | N.A. | N.A. | N.A. |
| DAC 230 | N.A. | N.A. | Adjustable | Adjustable | Adjustable | Adjustable |
| MUX 232 | B | B | A | A | A | A |
| Control 234 | High | High | Low | Low | Low | Low |
| Input 236 | High | Low | N.A. | N.A. | N.A. | N.A. |

Control signals for several of the above elements may come from a control block (not shown).

FIG. 6 illustrates, in both a more simplified and more specific manner, a circuit in accordance with another illustrative embodiment. In particular, a number of switches are omitted to provide easier analysis of circuit operation for a first polarity pulse that may form part of a constant current pulse train. The illustrative ICD 300 includes a positive high voltage +V 302 that is initially charged to a desired level. A first high side switch 304 is shown as an IGBT and is controlled by a first control block 306 which may use the output of the switch 304 to provide a reference for opening or closing the first switch 304. The first control block 306 also takes a control signal from operational circuitry C that controls the operation of the ICD. A second high side switch 310 is also shown, with a second control block 312 similar to the first control block 306. If so desired, the first and second high side switches 304, 310, may be replaced by silicon controlled rectifiers (SCR). If SCR devices are used for either or both of switches 304, 310, the control circuitry 306, 312 may be suitably modified.

Current from either of the high side switches 306 is directed to the patient 314 (shown as an impedance RP) via electrodes 316, 318. Current then goes to one of a first low side switch 320 or a second low side switch 328, which are each shown at IGBT devices. Control circuitry for the first low side switch is shown schematically as including an operational amplifier 322 and a DAC 324. The inverting input of the operational amplifier 322 is coupled to node 326, while the non-inverting input of the operational amplifier 322 is coupled to the output of the DAC 324. A resistor 330 couples node 326 to ground. Control circuitry for controlling the low side leg including low side switch 328 is omitted for simplicity; it can be seen from FIG. 5 that the use of a few switches allows the operational amplifier 320 and DAC 322 to be reused for both legs.

When a fibrillation inducing pulse train is desired, a first step is to charge a capacitor (not shown) used to provide +V 302. The capacitor may be charged to a level reasonably anticipated to allow a constant current output during application of the fibrillation inducing pulse train. With the capacitor charged, a control signal is supplied to the second control block 312 to close the second high side switch 310. At about the same time (or just earlier in time), the DAC 324 provides a signal to the operational amplifier 322 causing the operational amplifier 322 to provide a closing signal to the first low side switch 320.

With each of switches 310 and 320 closed, positive current follows a path from +V 302, through the second high side switch 310, to electrode 318 and into the patient, shown as impedance 314. The current is captured at electrode 316 and passes through the first low side switch 320 to node 326 and through the resistor 330 to ground/reference.

Initially, with no current flow, the operational amplifier 322 may provide a "HIGH" output, for example, by going directly to its rail voltage, essentially closing switch 320. Once current begins to flow through resistor 330, the voltage at node 326 rises in proportion to the amount of current flowing. As the voltage at node 326 rises, it begins to approach the output from the DAC 324. The voltage difference between node 326 and the output from the DAC 324 reaches a point where the operational amplifier 322 provides a reduced output to the first low side switch 320, causing the first low side switch 320 to modulate the current flowing therethrough. This all occurs quite quickly (typically within a few microseconds or less) and equilibrium is reached where the voltage at node 326 approximates the voltage output from the DAC 324. This configuration renders the low side leg including first low side switch 320 a constant current source, as long as the voltage +V 302 remains high enough such that the voltage drop across the patient 314, given the current flowing, allows the switch 320 to operate as an amplifier.

Those of skill in the art will readily understand operation making use of the first high side switch 304 and second low side switch 328 in like fashion will generate a constant current signal with an opposite sign.

Figure 7:
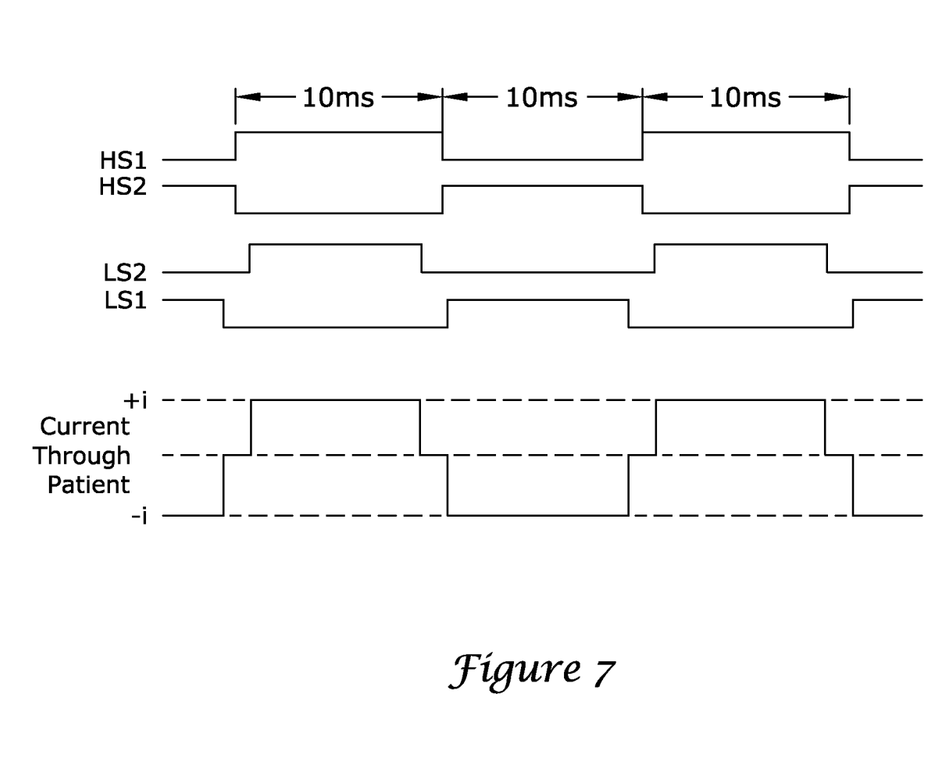
FIG. 7 graphically illustrates operation of an illustrative embodiment including switch on/off and output signal.

FIG. 7 graphically illustrates operation of an illustrative embodiment including switch on/off and output signal. The graph is divided into 10 millisecond intervals at the top. It can be seen that the high side switches are toggled every 10 milliseconds, with one switch closing and the other opening at about the same time. This gives a 20 millisecond period. The period can be selected as desired, for example, between 8 and 100 milliseconds, or between 16 and 40 milliseconds. The low side switches can be manipulated such that both are closed for a period of time before the high side switches are switched. Such a step is not required, but can be useful if there is a concern that a high side switch embodied as a silicon controlled rectifier (SCR) may remain open if current continues to flow through the switch even though it is powered down. In short, an SCR requires a minimum current flow to remain in a closed state allowing current flow, but also requires that current drop below the minimum level in order to shut off. The methods illustrated in U.S. patent application Ser. No. 10/011,957, filed Nov. 5, 2001 and now U.S. Pat. No. 6,952,608, the entire disclosure of which is incorporated herein by reference, can be used to assure positive turn-on of the high side switches.

As can be seen, the patient current is zero for a short time when both low side switches are closed, and is otherwise at either +I or −I, depending on the configuration of high and low side switches that not opened. If operating within a range of patient impedances including any predefined "worst-case" scenario impedances, the current will be constant regardless of the actual patient impedance for the duration of the fibrillation inducing signal.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. An implantable cardioverter defibrillator (ICD) comprising:
   a housing;
   therapy delivery electrodes; and
   circuitry contained within the housing and coupled to the therapy delivery electrodes, the circuitry including an energy storage system and a battery, the circuitry configured for generating defibrillation therapy using the energy storage system; wherein:
   the circuitry includes an H-bridge circuit having a high side and a low side, the high side having a first switch coupled to a first node and a second switch coupled to a second node, the first and second nodes being coupled to the therapy delivery electrodes, the low side comprising a third switch coupling the first node to a low node and a fourth switch coupling the second node to the low node, and control circuitry coupled to the first, second, third and fourth switches and configured to perform an induction sequence including successively engaging the switches in an alternating sequence to produce a controlled current alternating output between the therapy delivery electrodes;
   the low node is coupled to ground or reference for the circuit via a stimulus switch in parallel with a feedback resistor; and
   the H-bridge is coupled to a current modulation circuit including a transistor having current inlet node, a current outlet node, and a control node, the control node being coupled to a feedback circuit that takes an input signal from the low node and a control voltage from the control circuitry to modulate current flow through the feedback resistor while the stimulus switch is open during the induction sequence such that a substantially constant current is maintained for the controlled current alternating output.

2. The ICD of claim 1, wherein the control circuitry is configured to control timing of opening and closing the first, second, third and fourth switches such that the controlled current alternating current comprises a number of positive and negative pulses having substantially constant current magnitude.

3. The ICD of claim 2, wherein the control circuitry is configured such that the positive and negative pulses are separated by periods lacking either a positive or a negative pulse.

4. The ICD of claim 1, wherein the control circuitry is configured to perform the induction sequence by:
   at least partially charging the energy storage system; and
   discharging the energy storage system to create the controlled current alternating output.

5. The ICD of claim 4, wherein the control circuitry is configured such that the step of at least partially charging the energy storage system includes charging the energy storage system to a level more than sufficient to provide the controlled current alternating output for a time period sufficient to induce fibrillation.

6. An implantable cardioverter defibrillator (ICD) comprising:
   stimulus output electrodes configured for implantation in a patient;
   a battery subcircuit;
   an energy storage system including at least one capacitor;
   an H-bridge having a high side and a low side, each side having a first branch and a second branch, wherein current flow through the H-bridge is selectively controllable to deliver current to the output electrodes, further wherein the low side of the H-bridge is coupled to a current modulating circuit and a bypass switch;
   a controller coupled to the battery and the H-bridge; and
   a housing containing the battery subcircuit, energy storage system, H-bridge and controller;
   wherein the controller is configured to control delivery of at least defibrillation therapy to the output electrodes using the H-bridge, battery subcircuit and energy storage system by closing the bypass switch to disable the current modulating circuit of the H-bridge; and
   wherein the controller is also configured to operate using a fibrillation inducing mode to create an output of a controlled current alternating stimulus by:
   charging the energy storage system to at least a predetermined level;
   performing an alternating sequence of first and second delivery steps to deliver current to a patient via the electrodes using the branches of the high and low side of the H-bridge in alternating fashion; and
   during each delivery step of the fibrillation inducing mode, operating the current modulating circuit to ensure a constant current is delivered during each delivery step by opening the bypass switch to enable the current modulating circuit of the H-bridge.

* * * * *